United States Patent
Wu et al.

(10) Patent No.: US 9,643,001 B2
(45) Date of Patent: May 9, 2017

(54) WOUND CARE DRESSING

(71) Applicant: Taiwan Textile Research Institute, New Taipei (TW)

(72) Inventors: Ting-Yu Wu, New Taipei (TW); Ting-Yu Chang, New Taipei (TW)

(73) Assignee: Taiwan Textile Research Institute, New Taipei (TW)

( * ) Notice: Subject to any disclaimer, the term of this patent is extended or adjusted under 35 U.S.C. 154(b) by 0 days.

(21) Appl. No.: 15/013,997

(22) Filed: Feb. 2, 2016

(65) Prior Publication Data
US 2016/0303362 A1     Oct. 20, 2016

(30) Foreign Application Priority Data
Apr. 14, 2015 (TW) .............................. 104111968 A

(51) Int. Cl.
| | |
|---|---|
| *A61N 1/04* | (2006.01) |
| *A61N 1/20* | (2006.01) |
| *A61N 1/32* | (2006.01) |
| *A61L 15/42* | (2006.01) |
| *A61L 15/44* | (2006.01) |
| *A61L 15/60* | (2006.01) |

(52) U.S. Cl.
CPC .......... *A61N 1/0468* (2013.01); *A61L 15/42* (2013.01); *A61L 15/44* (2013.01); *A61L 15/60* (2013.01); *A61N 1/0496* (2013.01); *A61N 1/205* (2013.01); *A61L 2300/102* (2013.01); *A61L 2300/104* (2013.01); *A61L 2430/34* (2013.01)

(58) Field of Classification Search
CPC ...... A61N 1/0468; A61N 1/205; A61N 1/326; A61L 15/42; A61L 15/52; A61L 15/44
See application file for complete search history.

(56) References Cited

U.S. PATENT DOCUMENTS 8,224,439 B2 *   7/2012   Skiba ..................... A61N 1/303
                                                        607/1
9,511,215 B2 *   12/2016  Skiba ...................... A61N 1/30
(Continued)

FOREIGN PATENT DOCUMENTS

| CN | 1775301 | 5/2006 |
|---|---|---|
| CN | 102293698 | 12/2011 |

(Continued)

*Primary Examiner* — Catherine Voorhees
(74) *Attorney, Agent, or Firm* — Jianq Chyun IP Office

(57) ABSTRACT

A wound care dressing is provided, including a hydrophobic base fabric, a plurality of electrode pairs, a plurality of hydrogel layers, and a waterproof thin film. The hydrophobic base fabric has a first surface and a second surface opposite to each other. The electrode pairs are arranged in an array and disposed on the first surface of the hydrophobic base fabric. The hydrogel layers are not in contact with one other, and each hydrogel layer covers a top surface and side walls of each electrode in the electrode pairs. After the hydrogel layers are in contact with a wound and absorb tissue fluid from the wound, the hydrogel layers form a restrictive electronic cycling channel with the electrode pairs to establish a plurality of bioelectric fields promoting wound healing on a surface of the wound. The waterproof thin film is disposed on the second surface of the hydrophobic base fabric.

11 Claims, 5 Drawing Sheets

(56) References Cited

U.S. PATENT DOCUMENTS

| | | | |
|---|---|---|---|
| 2002/0062116 A1* | 5/2002 | Mizutani | A61F 13/4704 |
| | | | 604/385.28 |
| 2004/0267190 A1 | 12/2004 | Tamarkin et al. | |
| 2006/0200044 A1* | 9/2006 | Freeman | A61B 5/14532 |
| | | | 600/583 |
| 2006/0270942 A1* | 11/2006 | McAdams | A61B 5/0531 |
| | | | 600/547 |
| 2009/0018424 A1* | 1/2009 | Kamath | A61B 5/7235 |
| | | | 600/347 |
| 2012/0078153 A1 | 3/2012 | Russell et al. | |
| 2013/0172724 A1* | 7/2013 | Ali Mohamed Aziz | |
| | | | A61B 5/04087 |
| | | | 600/391 |
| 2014/0208464 A1* | 7/2014 | Chadwick | A61K 35/76 |
| | | | 800/301 |
| 2016/0059009 A1* | 3/2016 | Skiba | A61N 1/30 |
| | | | 602/53 |

FOREIGN PATENT DOCUMENTS

| | | |
|---|---|---|
| CN | 102600019 | 7/2012 |
| CN | 104225787 | 12/2014 |
| JP | 2014207987 | 11/2014 |
| WO | 2008114918 | 9/2008 |

* cited by examiner

WOUND CARE DRESSING

CROSS-REFERENCE TO RELATED APPLICATION

This application claims the priority benefit of Taiwan application serial no. 104111968, filed on Apr. 14, 2015. The entirety of the above-mentioned patent application is hereby incorporated by reference herein and made a part of this specification.

BACKGROUND OF THE INVENTION

Field of the Invention

The invention is related to a wound care dressing, and more particularly, to a wound care dressing capable of promoting wound healing.

Description of Related Art

In general, when a wound occurs on the skin, normal protective function cannot take place, and in the case of improper wound treatment, phenomenon such as inflammation due to infection from pathogens may result. Therefore, treating the wound with an accurate and suitable method is relatively important in terms of preventing infection to the wound and wound healing promotion.

In recent years, various dressings in wound care applications have been developed. Among commonly used dressing products, most promote wound healing via a method of electrical stimulation through a mechanism of cell proliferation by using an external power supply. However, since the current and the voltage supplied are too high, discomfort may occur to the patient and pain at the site of the wound may be increased. Moreover, among commonly used dressing products, most adopt silver electrode coating as antiseptic for direct contact with the wound, and although silver electrode coating has good sterilization function and can prevent inflammation to the wound, silver has cytotoxicity, and therefore damage to human cells occurs during sterilization.

Moreover, a moderately moist environment needs to be provided to facilitate wound healing. However, the contact surface of known dressings and the wound is often dry such that the wound and the dressing are tightly adhered. As a result, when the dressing on the surface of the wound is changed or removed, secondary damage occurs to the wound. Moreover, scar removal at the site of the wound is also an important issue in wound recovery; however, most known wound dressings do not have significant scar removal effect.

Based on the above, a wound care dressing superior in aspects such as moisture retention, anti bacteria, wound healing promotion, and scar removal is urgently needed.

SUMMARY OF THE INVENTION

The invention provides a wound care dressing capable of effectively promoting wound healing and having the effects of moisture retention, anti bacteria, and scar removal.

The invention provides a wound care dressing including a hydrophobic base fabric, a plurality of electrode pairs, a plurality of hydrogel layers, and a waterproof thin film. The hydrophobic base fabric has a first surface and a second surface opposite to each other. The plurality of electrode pairs is arranged in an array and disposed on the first surface of the hydrophobic base fabric. The plurality of hydrogel layers is not in contact with one other, and each of the hydrogel layers covers a top surface and side walls of each of the electrodes in the electrode pairs. After the hydrogel layers are in contact with a wound and absorb tissue fluid from the wound, the hydrogel layers form a restrictive electronic cycling channel with the electrode pairs to establish a plurality of bioelectric fields promoting wound healing on a surface of the wound. The waterproof thin film is disposed on the second surface of the hydrophobic base fabric.

In an embodiment of the invention, each of the electrode pairs includes a first electrode and a second electrode. The first electrode is formed by a first active substance and a first conductive carbon paste, wherein based on the total weight of the first active substance and the first conductive carbon paste, the content of the first conductive carbon paste is 5 wt % to 80 wt %. The second electrode is formed by a second active substance and a second conductive carbon paste, wherein based on the total weight of the second active substance and the second conductive carbon paste, the content of the second conductive carbon paste is 5 wt % to 80 wt %. When the wound care dressing is applied on a wound, the second electrode and the first electrode generate current conduction via the hydrogel layers.

In an embodiment of the invention, the material of the first active substance and the material of the second active substance include zinc, copper, silver, carbon, silver oxide, magnesium, manganese, nickel, or a combination thereof.

In an embodiment of the invention, the first electrode and the second electrode are respectively a symmetric semicircular electrode having the same size, the distance between the first electrode and the second electrode is 1.8 mm to 2.2 mm, and the radius of the semicircular electrode is 4.9 mm to 5.1 mm.

In an embodiment of the invention, the first electrode and the second electrode are respectively a circular electrode having the same size.

In an embodiment of the invention, the diameter of the circular electrode is 9.8 mm to 10.2 mm and the distance between the center points of adjacent first and second electrodes is 11 mm to 15 mm.

In an embodiment of the invention, the diameter of the circular electrode is 4.8 mm to 5.2 mm and the distance between the center points of adjacent first and second electrodes is 6 mm to 10 mm.

In an embodiment of the invention, each of the hydrogel layers is a UV curing layer including a main agent system, a UV curing initiator, and a polyol plasticizer. The main agent system includes acrylic acid, alkyl acrylate, fluoroalkyl ester, methacrylic acid, methyl methacrylate, 2-hydroxyethyl methacrylate, or glycidyl methacrylate. The UV curing initiator includes α-aminoketone, α-hydrocarbon ketone, acyl phosphate oxide, benzoin diethyl ether, benzophenone, a cationic photoinitiator, or benzoyl formate. The polyol plasticizer includes glycol, polyvinyl alcohol, polyvinylpyrrolidone, or glycerol.

In an embodiment of the invention, the thickness of each of the hydrogel layers is 1 mm to 2 mm.

In an embodiment of the invention, the thickness of each of the electrodes in the electrode pairs is 1.5 mm to 3 mm.

In an embodiment of the invention, the aperture of the hydrophobic base fabric is 5 μm to 40 μm, and the thickness of the hydrophobic base fabric is 0.5 mm to 1 mm.

In an embodiment of the invention, in the restrictive electronic cycling channel, the discharge voltage is 0.6 V to 0.9 V, and the current is 0.1 amperes to 0.3 amperes.

Based on the above, the invention provides a wound care dressing including a plurality of hydrogel layers having high water absorption, moisturizing properties, and antibacterial properties. Each of the hydrogel layers covers each of the electrodes in the electrode pairs, and after the hydrogel layers are in contact with the wound and absorb tissue fluid having the function of ionic conduction, the hydrogel layers form a restrictive electronic cycling channel with the electrode pairs to establish a plurality of bioelectric fields promoting wound healing on the surface of the wound. Therefore, in addition to effectively promoting wound healing, the wound care dressing provided by the invention also does not readily leave a scar at the wound, and further has the effects of moisture retention and anti bacteria.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
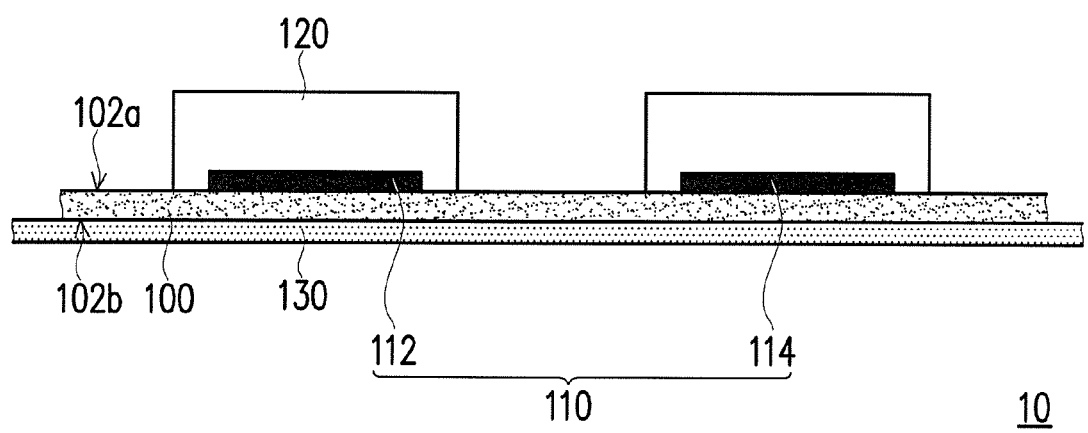
FIG. 1 is a cross-sectional schematic of a wound care dressing according to an embodiment of the invention.

FIG. 1 is a cross-sectional schematic of a wound care dressing according to an embodiment of the invention.

First, referring to FIG. 1, in the present embodiment, a wound care dressing 10 can include a hydrophobic base fabric 100, a plurality of electrode pairs 110 (for clarity, only one electrode pair is shown here, and the details of implementation relating to a plurality of electrode pairs are described later with reference to figures), a plurality of hydrogel layers 120, and a waterproof thin film 130. Moreover, although the cross-section of the hydrogel layers 120 in FIG. 1 are shown as rectangles having edges and corners for clarity, it can be understood that the hydrogel layers 120 in actuality have cross-sections of other shapes (such as an ellipse) due to natural forces such as surface tension and cohesion of the hydrogel itself.

Referring to FIG. 1, the hydrophobic base fabric 100 has a first surface 102*a* and a second surface 102*b* opposite to each other. In the present embodiment, since the electrode pairs 110 are formed on the hydrophobic base fabric 100 via a method of heating and coating, the material of the hydrophobic base fabric 100 has the feature of not shrinking readily in a high temperature environment, so as to prevent deviation to the position of the electrodes formed thereon via a method of heating, curing, and drying. Moreover, the hydrophobic properties of the hydrophobic base fabric 100 can make moisture only circulate between the hydrogel layers 120 and the electrode pairs 110. In the present embodiment, the hydrophobic base fabric 100 can include a porous nonwoven fabric such as polypropylene (PP), but the invention is not limited thereto, and other materials having hydrophobic properties that do not shrink readily in a high temperature environment can also be used. More specifically, the aperture of the hydrophobic base fabric 100 is, for instance, 5 μm to 40 μm, and the thickness is, for instance, 0.5 mm to 1 mm. When the aperture of the hydrophobic base fabric 100 is greater than the above range, deviation may occur to the position of the electrodes to be formed on the hydrophobic base fabric 100 due to higher volumetric shrinkage. Moreover, when the aperture is in the above range, moisture does not readily pass through the hydrophobic base fabric 100, and therefore the hydrophobic base fabric 100 has good hydrophobic effect.

Then, referring further to FIG. 1, the electrode pairs 110 are disposed on the first surface 102*a* of the hydrophobic base fabric 100. Each of the electrode pairs 110 can include a first electrode 112 and a second electrode 114. In the present embodiment, when the wound care dressing 10 is applied on a wound, after the hydrogel layers 120 absorb tissue fluid from the wound (containing $Na^+$ and $Cl^-$) having the function of ionic conduction, the second electrode 114 and the first electrode 112 can be in contact with the tissue fluid via the hydrogel layers 120, so as to generate current conduction according to the potential difference between the first electrode 112 and the second electrode 114, and thereby establish a plurality of bioelectric fields promoting wound healing on the surface of the wound.

In the present embodiment, the thickness of each of the first electrode 112 and the second electrode 114 in the electrode pairs 110 is, for instance, 1.5 mm to 3 mm. The first electrode 112 is formed by a first active substance and a conductive carbon paste, wherein based on a total weight of the first active substance and the conductive carbon paste, the content of the conductive carbon paste is, for instance, 5 wt % to 80 wt %, and preferably, the content of the conductive carbon paste is, for instance, 40 wt % to 60 wt %. The second electrode 114 is formed by a second active substance and a conductive carbon paste, wherein based on a total weight of the second active substance and the conductive carbon paste, the content of the conductive carbon paste is, for instance, 5 wt % to 80 wt %, and preferably, the content of the conductive carbon paste is, for instance, 40 wt % to 60 wt %. More specifically, the material of the first active substance is different from the material of the second active substance, and a potential difference exists between the two; therefore, the respectively formed first electrode 112 and second electrode 114 can generate current conduction. The material of the first active substance and the material of the second active substance can include zinc, copper, silver, carbon, silver oxide, magnesium, manganese, nickel, or a combination thereof, but the invention is not limited thereto. Moreover, the conductive carbon paste can facilitate electrical conduction of the first electrode 112 and the second electrode 114 and improve the electrical properties thereof.

Referring to FIG. 1, a plurality of hydrogel layers 120 cover a top surface and sidewalls of the first electrode 112 and the second electrode 114 in the electrode pairs 110, and the hydrogel layers 120 are not in contact with one another. If the hydrogel layers 120 were in contact with one another, a discharge reaction may be generated before contact with the wound, thus causing decay to the function of the electrode pairs 110. Moreover, since the hydrogel layers 120 cover the top surface and the sidewalls of the first electrode 112 and the second electrode 114 in the electrode pairs 110, the possibility of contact between the first electrode 112 and the second electrode 114 and air can be reduced, thus improving the stability of the first electrode 112 and the second electrode 114.

Then, referring further to FIG. 1, after the hydrogel layers 120 are in contact with the wound and absorb tissue fluid from the wound having the function of ionic conduction, the hydrogel layers 120 form a restrictive electronic cycling channel with the electrode pairs 110 to establish a plurality of bioelectric fields promoting wound healing on the surface of the wound. It should be mentioned that, in the restrictive electronic cycling channel formed by the hydrogel layers 120 and the electrode pairs 110, the discharge voltage is, for instance, 0.6 V to 0.9 V, and the current is, for instance, 0.1 amperes to 0.3 amperes. As a result, in comparison to the mechanism in prior art promoting wound healing via electrical stimulation through an external power supply, the discharge voltage and the current supplied by the wound care dressing of the invention are lower, and therefore the wound care dressing of the invention does not readily generate irritation to the human body, and still has excellent effect of wound healing promotion.

More specifically, the hydrogel layers 120 are, for instance, UV curing layers that do not readily shrink in a high-temperature reaction, and can include a main agent system, a UV curing initiator, and a polyol plasticizer. In the present embodiment, the main agent system can include acrylic acid, alkyl acrylate, fluoroalkyl ester, methacrylic acid, methyl methacrylate, 2-hydroxyethyl methacrylate, or glycidyl methacrylate. The UV curing initiator can include α-aminoketone, α-hydrocarbon ketone, acyl phosphate oxide, benzoin diethyl ether, benzophenone, a cationic photoinitiator, or benzoyl formate. The polyol plasticizer can include glycol, polyvinyl alcohol, polyvinylpyrrolidone, or glycerol. The polyol plasticizer can adjust the softness of the hydrogel layers 120, and has a shaping effect. However, the invention is not limited thereto, and other photopolymerizable materials that do not shrink readily in a high-temperature reaction can also be used to prepare the hydrogel layers 120. The thickness of each of the hydrogel layers 120 is, for instance, 1 mm to 2 mm, and the thickness of each of the hydrogel layers 120 can be adjusted according to the depth of the wound. The film strength of the hydrogel layers 120 is, for instance, 3 MPa to 4 MPa.

It should be mentioned that, since the hydrogel layers 120 instead of the electrode pair 110 are in contact with the wound, the electrode coating having cytotoxicity is not in direct contact with the wound. As a result, wound healing can be promoted in a method of electrical stimulation without causing damage to human cells. Moreover, since the hydrogel layers 120 have high water absorption and moisturizing properties, the wound can maintain suitable moisture to facilitate wound healing, and when the wound care dressing 10 is changed or removed, secondary damage does not occur to the wound. Moreover, the hydrogel layers 120 also have good anti-bacterial properties, and therefore can isolate outside harmful substances from contact with the wound, and thereby prevent infection or inflammation to the wound.

Referring further to FIG. 1, the waterproof thin film 130 is disposed on the second surface 102b of the hydrophobic base fabric 100. The material of the waterproof thin film 130 is, for instance, polyurethane having elasticity, and the thickness is, for instance, 0.1 mm to 0.5 mm. The waterproof thin film 130 can prevent contact between external water vapor or outside harmful substances and the wound. Therefore, the waterproof thin film 130 has the function of preventing infection or inflammation to the wound.

The manufacturing process of the wound care dressing 10 is described in detail in the following. First, the first active substance and the conductive carbon paste are uniformly mixed to prepare the material of the first electrode 112, and the second active substance and the conductive carbon paste are uniformly mixed to prepare the material of the second electrode 114. Then, the uniformly mixed first active substance and conductive carbon paste are screen printed on the first surface 102a of the hydrophobic base fabric 100 and thermal cured and dried under 60° C. to 80° C. for 30 minutes. Then, the uniformly mixed second active substance and conductive carbon paste are screen printed on the first surface 102a of the hydrophobic base fabric 100 and thermal cured and dried under 60° C. to 80° C. for 30 minutes. In this way, a plurality of electrode pairs 110 can be formed. Then, the materials (including the main agent system, the UV curing initiator, and the polyol plasticizer) of the hydrogel layers 120 are uniformly mixed and aligned and coated on the plurality of electrode pairs 110, and then cured via light irradiation (in the present embodiment, a UV light of 247 nm can be used to perform curing by irradiation for 60 seconds) to form the plurality of hydrogel layers 120 covering the top surface and the sidewalls of the first electrode 112 and the second electrode 114 in the electrode pairs 110. Lastly, the waterproof thin film 130 is aligned and adhered to the second surface 102b of the hydrophobic base fabric 100 to complete the manufacture of the wound care dressing 10.

Figure 2:
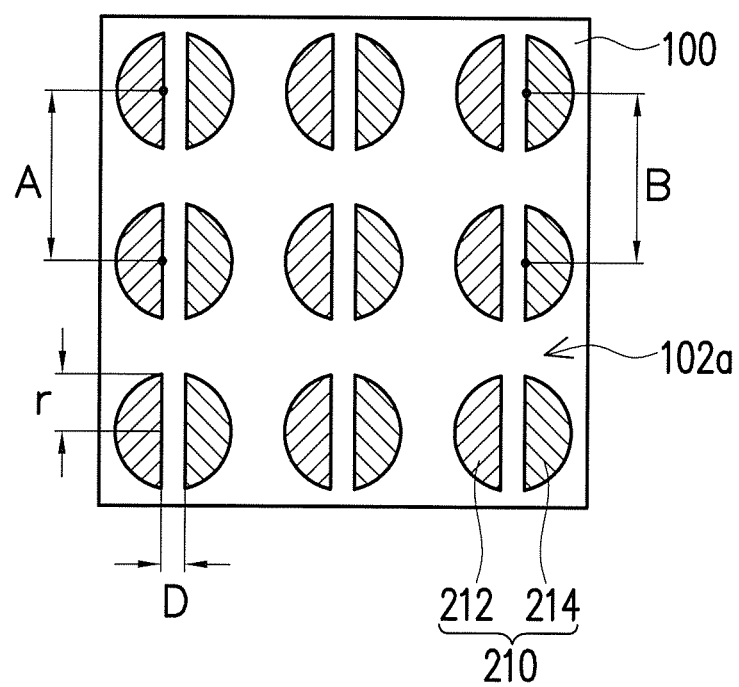
FIG. 2 is a top view of a wound care dressing according to the first embodiment of the invention.
Figure 3:
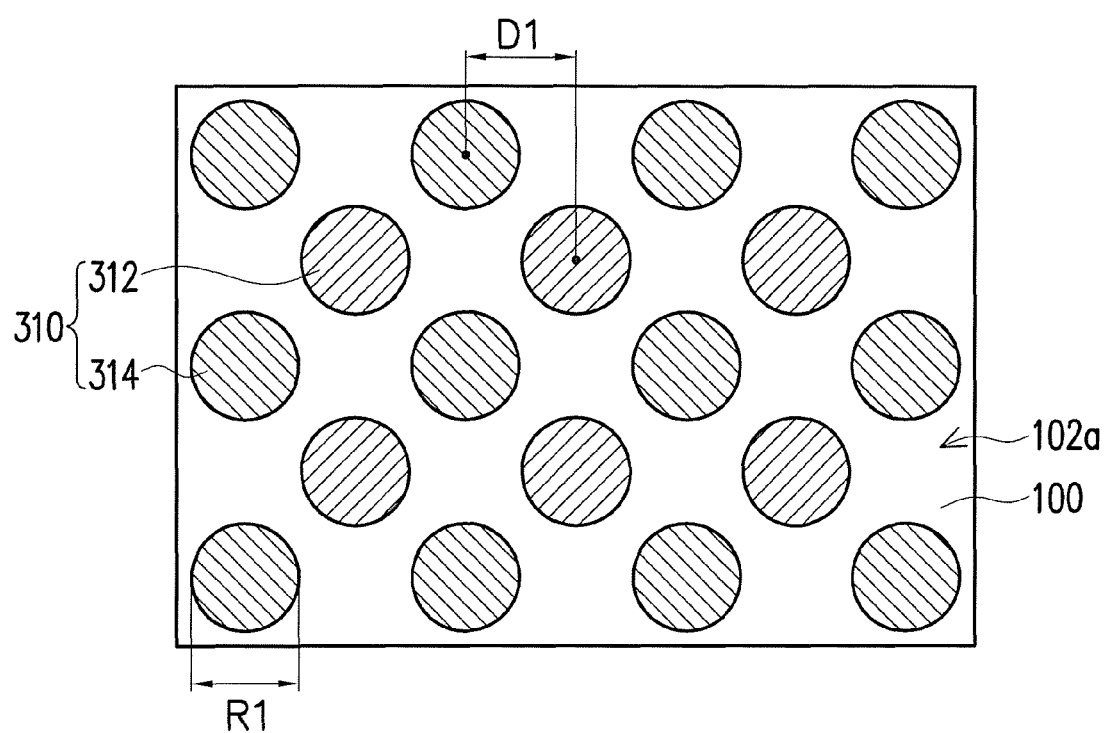
FIG. 3 is a top view of a wound care dressing according to the second embodiment of the invention.
Figure 4:
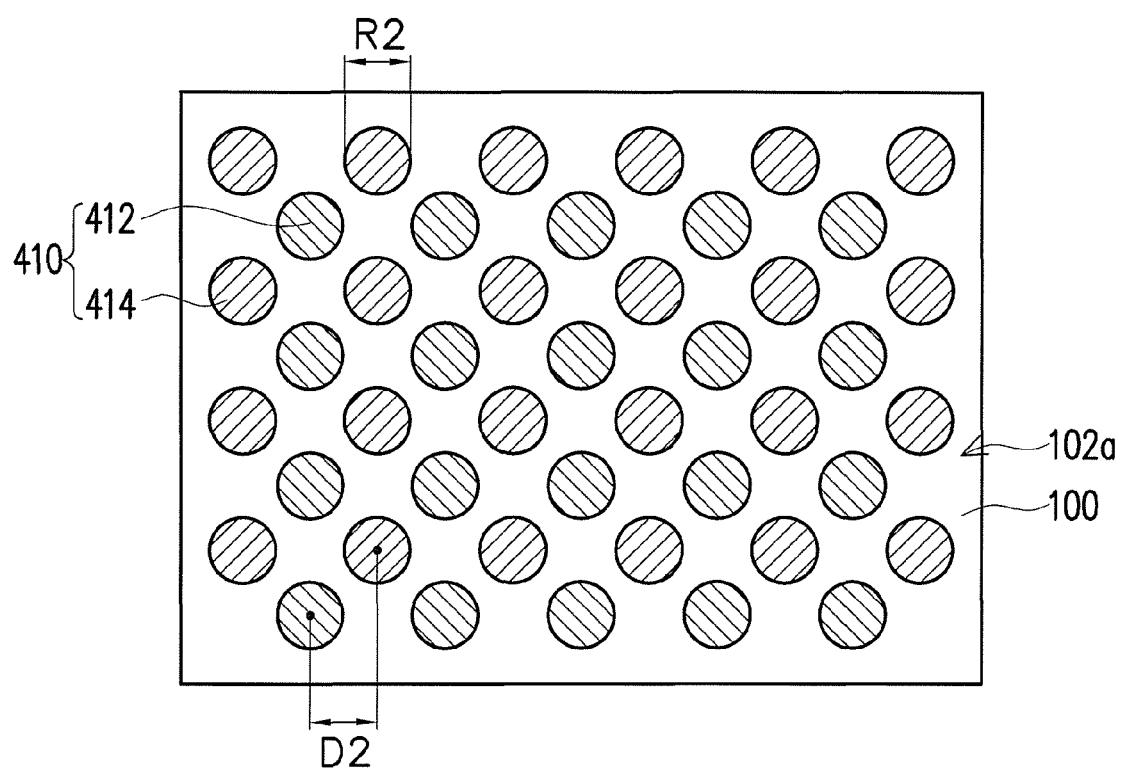
FIG. 4 is a top view of a wound care dressing according to the third embodiment of the invention.

FIG. 2 is a top view of a wound care dressing according to the first embodiment of the invention. FIG. 3 is a top view of a wound care dressing according to the second embodiment of the invention. FIG. 4 is a top view of a wound care dressing according to the third embodiment of the invention. FIG. 2, FIG. 3, and FIG. 4 are mainly used to explain the arrangement structures of the plurality of electrode pairs and the shape configurations of the first electrode and the second electrode in each of the electrode pairs, wherein for clarity, the hydrogel layers and the waterproof thin film are omitted.

The embodiments shown in FIG. 2, FIG. 3, and FIG. 4 are similar to the embodiment shown in FIG. 1, and therefore the same components are represented by the same reference numerals and are not repeated herein. More specifically, the electrode pairs 110 in FIG. 1 can be electrode pairs 210, 310, or 410 respectively shown in FIG. 2, FIG. 3, or FIG. 4, and the first electrode 112 and the second electrode 114 in FIG. 1 can be the first electrode 212 and the second electrode 214 in FIG. 2, the first electrode 312 and the second electrode 314 in FIG. 3, or the first electrode 412 and the second electrode 414 in FIG. 4. However, the following embodiments relating to the arrangement structures of the electrode pairs and the shape configurations of the first electrode and the second electrode are only exemplary, and the invention is not limited thereto.

Referring first to FIG. 2, the plurality of electrode pairs 210 is arranged in an array and disposed on the first surface 102a of the hydrophobic base fabric 100. Each of the electrode pairs 210 includes a first electrode 212 and a second electrode 214, and the material of each thereof is similar to that of each of the first electrode 112 and the second electrode 114, and is therefore not repeated herein. More specifically, the first electrode 212 and the second electrode 214 are respectively a symmetric semicircular electrode having the same size, wherein a distance D between the first electrode 212 and the second electrode 214 is, for instance, 1.8 mm to 2.2 mm, and a radius r of the semicircular electrode is, for instance, 4.9 mm to 5.1 mm. Moreover, a distance A between the centers of two adjacent first electrodes 212 is, for instance, 29.8 mm to 30.2 mm, a distance B between the centers of two adjacent second electrodes 214 is, for instance, 29.8 mm to 30.2 mm, and the distance A is, for instance, equal to the distance B.

Referring to FIG. 3, the plurality of electrode pairs 310 is arranged in an array and disposed on the first surface 102*a* of the hydrophobic base fabric 100. Each of the electrode pairs 310 includes a first electrode 312 and a second electrode 314, and the material of each thereof is similar to that of each of the first electrode 112 and the second electrode 114, and is therefore not repeated herein. More specifically, the first electrode 312 and the second electrode 314 are respectively a circular electrode having the same size, wherein a diameter R1 of the circular electrode is, for instance, 9.8 mm to 10.2 mm, and a distance D1 between the center points of adjacent first electrode 312 and second electrode 314 (i.e., the center of each of the first electrode 312 and the second electrode 314) is, for instance, 11 mm to 15 mm.

Referring to FIG. 4, the plurality of electrode pairs 410 is arranged in an array and disposed on the first surface 102*a* of the hydrophobic base fabric 100. Each of the electrode pairs 410 includes a first electrode 412 and a second electrode 414, and the material of each thereof is similar to that of each of the first electrode 112 and the second electrode 114, and is therefore not repeated herein. More specifically, the first electrode 412 and the second electrode 414 are respectively a circular electrode having the same size, wherein a diameter R2 of the circular electrode is, for instance, 4.8 mm to 5.2 mm, and a distance D2 between the center points of adjacent first electrode 412 and second electrode 414 (i.e., the center of each of the first electrode 412 and the second electrode 414) is, for instance, 6 mm to 10 mm.

In the following, the wound care dressing provided in the above embodiments and the properties thereof are described in detail via experimental examples. However, the following experimental examples are not intended to limit the invention.

EXPERIMENTAL EXAMPLES

To prove that the wound care dressing provided in the invention has excellent effect of wound healing promotion and does not readily leave a scar at the wound, the following experimental examples are provided.

It should be mentioned that, since the preparation process of the wound care dressing is described in detail above, descriptions of a portion of the preparation details of the wound care dressing are omitted for ease of explanation.

Preparation of Wound Care Dressing

Example 1

100 phr of conductive carbon paste and 10 phr of silver (as the material of the first active substance) were uniformly mixed to prepare a first electrode. 50 phr of conductive carbon paste and 10 phr of zinc (as the material of the second active substance) were uniformly mixed to prepare a second electrode. The formed plurality of electrode pairs was arranged in an array on the first surface of the hydrophobic base fabric in the arrangement structure and the electrode shape shown in FIG. 4. Then, the materials of the hydrogel layers were uniformly mixed and aligned and coated on the plurality of electrode pairs in a unit spray amount of 0.5 ml, and then curing was performed by irradiating a UV light at 247 nm for 60 seconds to form hydrogel layers each having a thickness of 1 mm to 2 mm. Lastly, the waterproof thin film was aligned and adhered to the second surface of the hydrophobic base fabric to complete the manufacture of the wound care dressing.

Example 2

100 phr of conductive carbon paste and 10 phr of silver (as the material of the first active substance) were uniformly mixed to prepare a first electrode. 100 phr of conductive carbon paste and 10 phr of zinc (as the material of the second active substance) were uniformly mixed to prepare a second electrode. The formed plurality of electrode pairs was arranged in an array on the first surface of the hydrophobic base fabric in the arrangement structure and the electrode shape shown in FIG. 2. Then, the materials of the hydrogel layers were uniformly mixed and aligned and coated on the plurality of electrode pairs in a unit spray amount of 1 ml, and then curing was performed by irradiating a UV light at 247 nm for 60 seconds to form hydrogel layers each having a thickness of 1 mm to 2 mm. Lastly, the waterproof thin film was aligned and adhered to the second surface of the hydrophobic base fabric to complete the manufacture of the wound care dressing.

Example 3

100 phr of conductive carbon paste and 10 phr of silver (as the material of the first active substance) were uniformly mixed to prepare a first electrode. 50 phr of conductive carbon paste and 10 phr of zinc (as the material of the second active substance) were uniformly mixed to prepare a second electrode. The formed plurality of electrode pairs was arranged in an array on the first surface of the hydrophobic base fabric in the arrangement structure and the electrode shape shown in FIG. 2. Then, the materials of the hydrogel layers were uniformly mixed and aligned and coated on the plurality of electrode pairs in a unit spray amount of 1 ml, and then curing was performed by irradiating a UV light at 247 nm for 60 seconds to form hydrogel layers each having a thickness of 1 mm to 2 mm. Lastly, the waterproof thin film was aligned and adhered to the second surface of the hydrophobic base fabric to complete the manufacture of the wound care dressing.

Example 4

100 phr of conductive carbon paste and 10 phr of silver (as the material of the first active substance) were uniformly mixed to prepare a first electrode. 25 phr of conductive carbon paste and 10 phr of zinc (as the material of the second active substance) were uniformly mixed to prepare a second electrode. The formed plurality of electrode pairs was arranged in an array on the first surface of the hydrophobic base fabric in the arrangement structure and the electrode shape shown in FIG. 2. Then, the materials of the hydrogel layers were uniformly mixed and aligned and coated on the plurality of electrode pairs in a unit spray amount of 1 ml, and then curing was performed by irradiating a UV light at 247 nm for 60 seconds to form hydrogel layers each having a thickness of 1 mm to 2 mm. Lastly, the waterproof thin film was aligned and adhered to the second surface of the hydrophobic base fabric to complete the manufacture of the wound care dressing.

Example 5

100 phr of conductive carbon paste and 10 phr of silver (as the material of the first active substance) were uniformly mixed to prepare a first electrode. 10 phr of conductive carbon paste and 10 phr of zinc (as the material of the second active substance) were uniformly mixed to prepare a second electrode. The formed plurality of electrode pairs was arranged in an array on the first surface of the hydrophobic base fabric in the arrangement structure and the electrode shape shown in FIG. 2. Then, the materials of the hydrogel layers were uniformly mixed and aligned and coated on the plurality of electrode pairs in a unit spray amount of 1 ml, and then curing was performed by irradiating a UV light at 247 nm for 60 seconds to form hydrogel layers each having a thickness of 1 mm to 2 mm. Lastly, the waterproof thin film was aligned and adhered to the second surface of the hydrophobic base fabric to complete the manufacture of the wound care dressing.

Comparative Example 1

Gauze (commercial product; trade name: sterile nonwoven fabric gauze pad, made by Yoho Medical).

Comparative Example 2

Hydrogel dressing (commercial product; trade name: Harrison dressing hydrogel surgical wound dressing, made by Amed Co., Ltd.)
Evaluation of Wound Healing Promotion and Effect of Scar Removal Then, the wound care dressing of each of Example 1 to Example 5, the gauze of Comparative Example 1, and the hydrogel dressing of Comparative Example 2 were evaluated for wound healing promotion and effect of scar removal via the following methods.

In the present experiment, a burn test was performed on rats with a copper block at 120° C. for 30 seconds. Via this step, a wound having a size of about 0.8 cm² occurred to the back of each of the rats. Then, the wound care dressing of each of Example 1 to Example 5, the gauze of Comparative Example 1, and the hydrogel dressing of comparative Example 2 were respectively applied on the wound of each of the rats and were changed every 8 hours.

During the experiment, the healing of the wounds was observed via the naked eye, and the efficiency of wound healing promotion was calculated via the following equation:

$$\text{Efficiency of wound healing promotion} = \frac{(\text{Healing time of gauze} - \text{healing time of example})}{\text{Healing time of gauze}} \times 100\%$$

Figure 5:
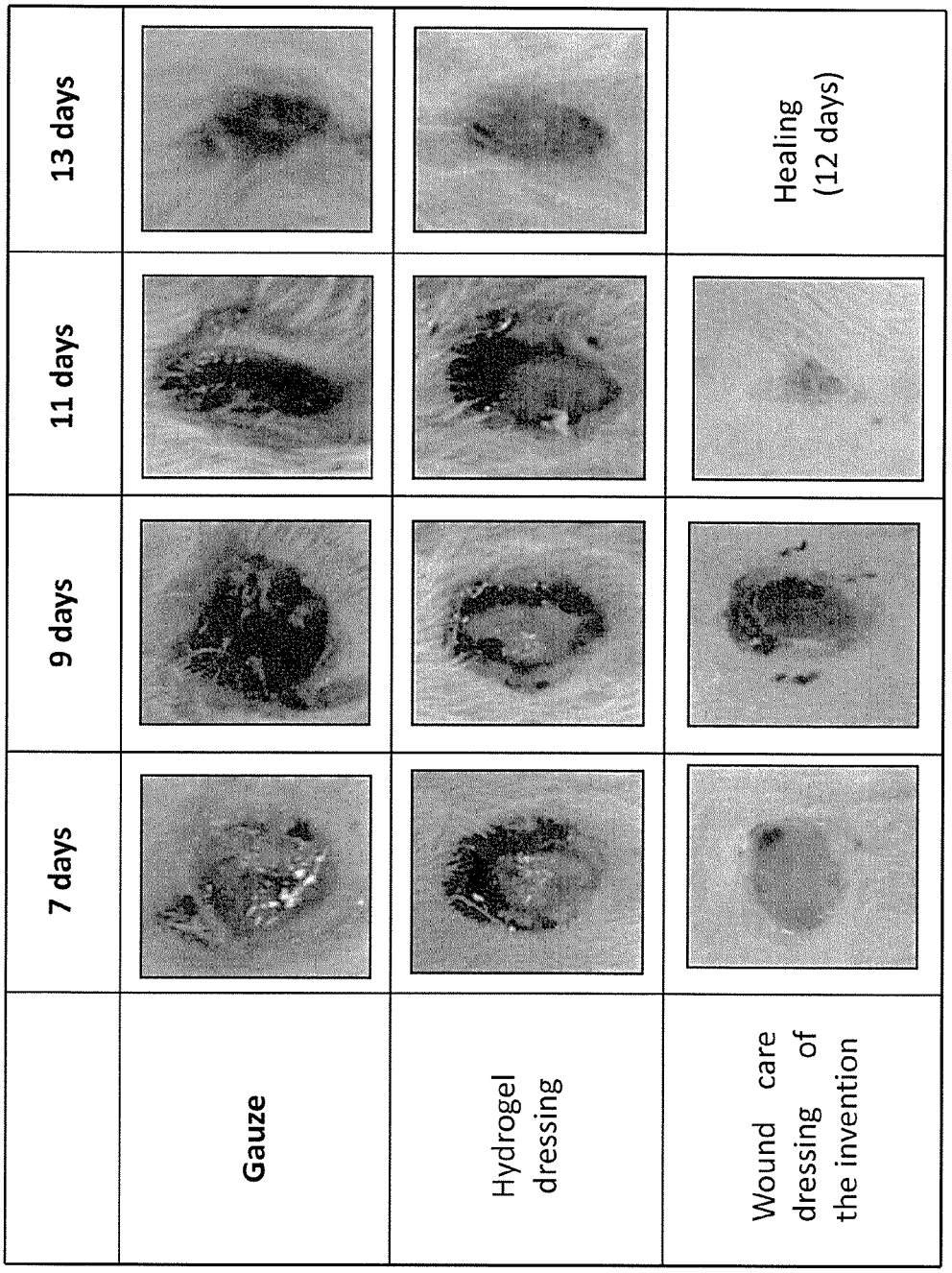
FIG. 5 shows test results of wound care dressings in animal experiments according to an embodiment of the invention.

In particular, the healing time is the time needed for complete healing of the wounds. At the same time, a cytotoxicity test was performed via an ISO10993-5 test method, and a skin irritation test and a skin sensitivity test were performed via an ISO10993-10 test method. The experiment results are shown in FIG. 5 and Table 1 below.

TABLE 1

| | Wound coverage percentage (%) | Cytotoxicity | Skin sensitivity | Skin irritation | Healing time (days) | Efficiency of healing promotion (%) |
|---|---|---|---|---|---|---|
| Example 1 | 31.4 | 0 | 0 | 0 | 16 | 24 |
| Example 1 | 52 | 0 | 0 | 0 | 13 | 38 |
| Example 2 | 118 | 0 | 0 | 0 | 15 | 29 |
| Example 3 | 118 | 0 | 0 | 0 | 15 | 29 |
| Example 4 | 118 | 0 | 0 | 0 | 13 | 38 |
| Example 5 | 118 | 0 | 0 | 0 | 12 | 55 |
| Comparative Example 1 | 100 | 0 | 0 | 0 | 21 | 0 |
| Comparative Example 2 | 100 | 0 | 0 | 0 | 19 | 14 |

It can be known from Table 1 that, none of the wound care dressings of Example 1 to Example 5, the gauze of Comparative Example 1, and the hydrogel dressing of Comparative Example 2 presents cytotoxicity, skin sensitivity, and skin irritation to the experiment animals.

It can be known from Table 1 that, in terms of healing time, the gauze of Comparative Example 1 requires a time of 21 days to completely heal the wound when applied on the wound of the rat. The hydrogel dressing of Comparative Example 2 requires a time of 19 days to completely heal the wound when applied on the wound of the rat, and has an efficiency of healing promotion of 14%.

In comparison, Example 1 is the wound care dressing provided in the invention. It can be known from Table 1 that, when the wound care dressing of Example 1 is applied on the wound of the rat, in the case of a wound coverage percentage of 31.4% (2 electrode pairs acting on the surface of the wound), a time of 16 days is needed to completely heal the wound, and the efficiency of healing promotion is 24%; in the case of a wound coverage percentage of 52% (4 electrode pairs acting on the surface of the wound), a time of 13 days is needed to completely heal the wound, and the efficiency of healing promotion is 38%. Therefore, in comparison to the gauze of Comparative Example 1 and the hydrogel dressing of Comparative Example 2, the wound care dressing of Example 1 shortens the time needed for complete wound healing, and the efficiency of healing promotion is also greater. That is, via the wound care dressing provided in the invention, wound healing can be effectively promoted. Moreover, the greater the wound coverage percentage of the wound care dressing, the greater the number of electrode pairs acting on the surface of the wound. As a result, the effect of wound healing promotion is more significant.

In comparison, Examples 2 to 5 are the wound care dressing provided in the invention. It can be known from Table 1 that, when the wound care dressing of each of Examples 2 to 5 is applied on the wounds of the rats, in the case of a wound coverage percentage of 118%, the time of wound healing is respectively 15 days, 15 days, 13 days, and 12 days, and the efficiency of healing promotion is respectively 29%, 29%, 38%, and 55%. Therefore, in comparison to the gauze of Comparative Example 1 and the hydrogel dressing of Comparative Example 2, the wound care dressing of each of Examples 2 to 5 shortens the time needed for complete wound healing, and the efficiency of healing promotion is also greater. That is, via the wound care dressing provided in the invention, wound healing can be effectively promoted.

Then, referring to FIG. 5, the test results of the gauze of Comparative Example 1, the hydrogel dressing of Comparative Example 2, and the wound care dressing of Example 5 applied on the wounds of the rats after 7 days, 9 days, 11 days, and 13 days are shown. In comparison to the gauze of Comparative Example 1 and the hydrogel dressing of Comparative Example 2, the wound care dressing of Example 5 shows significant effect of wound healing promotion both after 7 days and 9 days. Moreover, after the gauze of Comparative Example 1 and the hydrogel dressing of Comparative Example 2 are applied on the wounds of the rats after 11 days, significant wound is still observed. In comparison, the wound to which the wound care dressing of Example 5 is applied is almost completely healed after 11 days. Therefore, it can be known that the wound care dressing provided in the invention has significant effect of wound healing promotion.

It should be mentioned that, after the gauze of Comparative Example 1 and the hydrogel dressing of Comparative Example 2 were used on the wounds of the rats for 13 days, although the effect of wound healing promotion was observed, the site of wound healing was spindle-shaped. In comparison, after the wound care dressing of Example 5 was used for 7 days and 9 days, the site of wound healing had a circular shape. In other words, the wound can heal uniformly and the healing rate is consistent by using the wound care dressing of Example 5. Therefore, it can be known that the wound care dressing provided in the invention does not readily leave a scar at the wound site and has good effect of scar removal.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A wound care dressing, comprising:
    a hydrophobic base fabric having a first surface and a second surface opposite to each other;
    a plurality of electrode pairs disposed on the first surface of the hydrophobic base fabric, wherein the electrode pairs are arranged in an array;
    a plurality of hydrogel layers, wherein the hydrogel layers are not in contact with one another, and each of the hydrogel layers covers a top surface and sidewalls of each of the electrodes in the electrode pairs, wherein after the hydrogel layers are in contact with a wound and absorb a tissue fluid from the wound, the hydrogel layers are adapted to form a restrictive electronic cycling channel with the electrode pairs to establish a plurality of bioelectric fields promoting wound healing on a surface of the wound; and
    a waterproof thin film disposed on the second surface of the hydrophobic base fabric,
    wherein each of the electrode pairs comprises:
        a first electrode formed by a first active substance and a first conductive carbon paste, wherein based on a total weight of the first active substance and the first conductive carbon paste, a content of the first conductive carbon paste is 5 wt % to 80 wt %; and
        a second electrode formed by a second active substance and a second conductive carbon paste, wherein based on a total weight of the second active substance and the second conductive carbon paste, a content of the second conductive carbon paste is 5 wt % to 80 wt %, and when the wound care dressing is applied on the wound, the second electrode and the first electrode generate a current conduction via at least the hydrogel layers.

2. The wound care dressing of claim 1, wherein a material of the first active substance and a material of the second active substance comprise zinc, copper, silver, carbon, silver oxide, magnesium, manganese, nickel, or a combination thereof.

3. The wound care dressing of claim 1, wherein the first electrode and the second electrode are respectively a symmetric semicircular electrode having a same size, a distance between the first electrode and the second electrode is 1.8 mm to 2.2 mm, and a radius of the semicircular electrode is 4.9 mm to 5.1 mm.

4. The wound care dressing of claim 1, wherein the first electrode and the second electrode are respectively a circular electrode having a same size.

5. The wound care dressing of claim 4, wherein a diameter of the circular electrode is 9.8 mm to 10.2 mm and a distance between center points of adjacent first and second electrodes is 11 mm to 15 mm.

6. The wound care dressing of claim 4, wherein a diameter of the circular electrode is 4.8 mm to 5.2 mm and a distance between center points of adjacent first and second electrodes is 6 mm to 10 mm.

7. The wound care dressing of claim 1, wherein each of the hydrogel layers is a UV curing layer comprising:
    a main agent system comprising acrylic acid, alkyl acrylate, fluoroalkyl ester, methacrylic acid, methyl methacrylate, 2-hydroxyethyl methacrylate, or glycidyl methacrylate;
    a UV curing initiator comprising α-aminoketone, α-hydrocarbon ketone, acyl phosphate oxide, benzoin diethyl ether, benzophenone, a cationic photoinitiator, or benzoyl formate; and
    a polyol plasticizer comprising glycol, polyvinyl alcohol, polyvinylpyrrolidone, or glycerol.

8. The wound care dressing of claim 1, wherein a thickness of each of the hydrogel layers is 1 mm to 2 mm.

9. The wound care dressing of claim 1, wherein a thickness of each of the electrodes in the electrode pairs is 1.5 mm to 3 mm.

10. The wound care dressing of claim 1, wherein an aperture of the hydrophobic base fabric is 5 μm to 40 μm, and a thickness of the hydrophobic base fabric is 0.5 mm to 1 mm.

11. The wound care dressing of claim 1, wherein in the restrictive electronic cycling channel, a discharge voltage of the restrictive electronic cycling channel formed by the hydrogel layers with the electrode pairs is 0.6 V to 0.9 V, and a current of the restrictive electronic cycling channel formed by the hydrogel layers with the electrode pairs is 0.1 amperes to 0.3 amperes.

* * * * *